United States Patent
Song et al.

(10) Patent No.: US 12,398,433 B2
(45) Date of Patent: *Aug. 26, 2025

(54) METHOD FOR IDENTIFYING SPECIES OF EUKARYOTE ON BASIS OF WHOLE GENOME ANALYSIS, AND USE THEREOF

(71) Applicant: INSTITUTE OF MEDICINAL PLANT DEVELOPMENT, CHINESE ACADEMY OF MEDICAL SCIENCES, Beijing (CN)

(72) Inventors: Jingyuan Song, Beijing (CN); Guihong Qi, Beijing (CN); Wenjie Xu, Beijing (CN); Lijun Hao, Beijing (CN); Yutong Gan, Beijing (CN); Tianyi Xin, Beijing (CN)

(73) Assignee: Institute Of Medicinal Plant Development, Chinese Academy Of Medical Sciences, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/269,902

(22) PCT Filed: Mar. 30, 2022

(86) PCT No.: PCT/CN2022/083950
§ 371 (c)(1),
(2) Date: Feb. 12, 2024

(87) PCT Pub. No.: WO2023/024508
PCT Pub. Date: Mar. 2, 2023

(65) Prior Publication Data
US 2024/0301516 A1    Sep. 12, 2024

(51) Int. Cl.
*C12Q 1/6895* (2018.01)
*C12Q 1/6811* (2018.01)
*C12Q 1/6888* (2018.01)
*G16B 20/00* (2019.01)
*G16B 30/10* (2019.01)

(52) U.S. Cl.
CPC .......... *C12Q 1/6895* (2013.01); *C12Q 1/6811* (2013.01); *C12Q 1/6888* (2013.01); *G16B 20/00* (2019.02); *G16B 30/10* (2019.02)

(58) Field of Classification Search
CPC .. C12Q 1/6895; C12Q 1/6811; C12Q 1/6888; G16B 20/00; G16B 30/10
See application file for complete search history.

(56) References Cited

U.S. PATENT DOCUMENTS

2023/0193301 A1* 6/2023 Song .................. C12N 15/8213
                                                          800/278

FOREIGN PATENT DOCUMENTS

| CN | 104830970 A | 8/2015 |
|---|---|---|
| CN | 104946730 A | 9/2015 |
| CN | 106446597 A | 2/2017 |
| CN | 106845151 A | 6/2017 |
| CN | 109680053 A | 4/2019 |
| CN | 110982888 A | 4/2020 |
| CN | 112080577 A | 12/2020 |
| CN | 113817857 A | 12/2021 |
| CN | 113897415 A | 1/2022 |
| CN | 115087750 B | 5/2023 |
| WO | 2015097030 A1 | 7/2015 |

OTHER PUBLICATIONS

Wang Z. CRISPR-Cas system for biomedical diagnostic platforms. View 1: 2020008, pp. 1-22. (Year: 2020).*
Jacobsen T. Characterization of Cas12a nucleases reveals diverse PAM profiles between closely-related orthologs. Nucleic Acids Research 48(10: 5624-5638. (Year: 2020).*
Kelley DR. Quake: quality-aware detection and correction of sequencing errors. Genome Biology 11(R116): pp. 1-13. (Year: 2010).*
Xiao G. Identification of *Mycobacterium abscessus* species and subspecies using the Cas 12a/sgRNA-based nucleic acid detection platform. European Journal of Clinical Microbiology and Infectious Diseases 39: 551-558. (Year: 2020).*
Liu Y. Detection of Ophiocordyceps sinensis and its common adulterates using species-specific primers. Frontiers in Microbiology 8 (1179): 1-7. (Year: 2017).*
Hua K. Estimating the total genome length of a metagenomic sample using k-mers. BMC Genomics 20(Suppl 2): 183, pp. 93-101. (Year: 2019).*
Korean Patent Application 2024-7007138, Office Action, issued Aug. 29, 2024.
Xiyi Ren et al., Sequencing and Functional Annotation of the Whole Genome of Shiraia bambusicola, Genome Report, G3 Genes/Genomes/Genetics, 10(1), p. 23-35, 2020, https://academic.oup.com/g3journal/article/10/1/23/6020313 by guest on May 13, 2024.
Shi-Yuan Li et al., CRISPR-Cas12a-assisted nucleic Acid Detection, Cell Discovery, 4:20, pp. 1-4, 2018.
PCT Patent Application No. PCT/CN2022/083950 International Search Report and Written Opinion issued on Jan. 3, 2023.
Chinese Patent Application No. 202280002592.3 Decision to Grant issued Mar. 12, 2023.

(Continued)

*Primary Examiner* — Olivia M. Wise
*Assistant Examiner* — Robert J. Kallal
(74) *Attorney, Agent, or Firm* — Erise IP, P.A.

(57) ABSTRACT

Disclosed in the present application are a method for identifying the species of a eukaryotic sample on the basis of whole genome analysis, and the use thereof, wherein the species identification of a sample to be detected is achieved by means of a species-specific target sequence obtained by screening. The species identification method of the present invention has good specificity, high sensitivity and good repeatability, and can achieve rapid species identification without relying on large-scale professional instruments.

10 Claims, 2 Drawing Sheets

Specification includes a Sequence Listing.

(56) References Cited

OTHER PUBLICATIONS

Chinese Patent Application No. 202280002592.3 Office Action issued Dec. 2, 2022.
Kittisak Buddhachat, et al. Bar-cas12a, a novel and rapid method for plant species of *Phyllantus amarus* Schumach. & Thonn, Scientific Reports, 11:20888, 2021.
Shi-Yuan Li, et al., "CRISPR-Cas12a-assisted nucleic acid detection," Cell Discovery, 4:20, 2018.
Yang You, et al., "Research Progress in CRISPR-Cas-Based Nucleic Acid Detection," Mil Med Sci, vol. 45, No. 12, Dec. 2021.

* cited by examiner

Fig. 1

| Species | Total potential target sequences | Potential target sequences after removing duplicates | Single copy potential target sequences | Average distance between two target sequences (bp) | Genome length |
|---|---|---|---|---|---|
| Ophiocordyceps sinensis | 3432386 | 1385096 | 1122151 | 33.08 | 113540554 |
| Cervus elaphus | 121153505 | 94378541 | 91710281 | 24.12 | 2922686136 |
| Rheum officinale | 7995 | 6685 | 5375 | 20.15 | 161094 |

Fig. 2

| Species | Target sequence | crRNA matched with target sequence |
|---|---|---|
| Ophiocordyceps sinensis | TTTGGGAGTGGTGACTCGATAATGA (SEQ ID NO:1) | UAAUUUCUACUAAGUGUAGAUGGAGUGGUGACUCGAUAAUGA (SEQ ID NO:13) |
| Cervus elaphus | TTTATGCACCTGATGATTTTCTACG (SEQ ID NO:3) | UAAUUUCUACUAAGUGUAGAUUGCACCUGAUGAUUUUCUACG (SEQ ID NO:15) |
| Rheum officinale | TTTCAATAATCGATTCGATCAAAAT (SEQ ID NO:18) | UAAUUUCUACUAAGUGUAGAUAAUAAUCGAUUCGAUCAAAAU (SEQ ID NO:14) |

Fig. 3

| Species being identified | Related species | Specificity analysis (5 or less of base mismatch numbers) |
|---|---|---|
| Ophiocordyceps sinensis | Cordyceps militaris | No similar sequence with base mismatch number ≤5 |
| Cervus elaphus | Rangifer tarandus | There are 14 similar sequences when the base mismatch number is 4, and there are 136 similar sequences when the base mismatch number is 5 |
| Rheum officinale | Rheum palmatum | No similar sequence with base mismatch number ≤5 |

SEQUENCE LISTING

```
<160> NUMBER OF SEQ ID NOS: 17

<210> SEQ ID NO 1
<211> LENGTH: 25
<212> TYPE: DNA
<213> ORGANISM: Ophiocordyceos sinensis

<400> SEQUENCE: 1
tttgggagtg gtgactcgat aatga                                       25
```

<210> SEQ ID NO 2
<211> LENGTH: 25
<212> TYPE: DNA
<213> ORGANISM: Rheum officinale

<400> SEQUENCE: 2
aatatggtta tgttatatta ataaa                                              25

<210> SEQ ID NO 3
<211> LENGTH: 25
<212> TYPE: DNA
<213> ORGANISM: Cervus elaphus

<400> SEQUENCE: 3
tttatgcacc tgatgattttt ctacg                                             25

<210> SEQ ID NO 4
<211> LENGTH: 22
<212> TYPE: DNA
<213> ORGANISM: Artificial Sequence
<220> FEATURE:
<223> OTHER INFORMATION: Forward amplification primer for the specific
      target sequence of Ophiocordyceos sinensis

<400> SEQUENCE: 4
ggaagtaaaa gtcgtaacaa gg                                                 22

<210> SEQ ID NO 5
<211> LENGTH: 20
<212> TYPE: DNA
<213> ORGANISM: Artificial Sequence
<220> FEATURE:
<223> OTHER INFORMATION: Reverse amplification primer for the specific
      target sequence of Ophiocordyceos sinensis

<400> SEQUENCE: 5
tcctccgctt attgatatgc                                                    20

<210> SEQ ID NO 6
<211> LENGTH: 21
<212> TYPE: DNA
<213> ORGANISM: Artificial Sequence
<220> FEATURE:
<223> OTHER INFORMATION: Forward amplification primer for the specific
      target sequence of Rheum officinale

<400> SEQUENCE: 6
ccaaattgcc cgaagcctat g                                                  21

<210> SEQ ID NO 7
<211> LENGTH: 20
<212> TYPE: DNA
<213> ORGANISM: Artificial Sequence
<220> FEATURE:
<223> OTHER INFORMATION: Reverse amplification primer for the specific
      target sequence of Rheum officinale

<400> SEQUENCE: 7
atcgctttcc gacccacaat                                                    20

<210> SEQ ID NO 8
<211> LENGTH: 20
<212> TYPE: DNA
<213> ORGANISM: Artificial Sequence
<220> FEATURE:
<223> OTHER INFORMATION: Forward amplification primer for the specific target sequence of Cervus elaphus

<400> SEQUENCE: 8
agcagaagtg atggttgctg                                                     20

<210> SEQ ID NO 9
<211> LENGTH: 22
<212> TYPE: DNA
<213> ORGANISM: Artificial Sequence
<220> FEATURE:
<223> OTHER INFORMATION: Reverse amplification primer for the specific
      target sequence of Cervus elaphus

<400> SEQUENCE: 9
aagaatccta ggaagaactg gt                                                  22

<210> SEQ ID NO 10
<211> LENGTH: 4
<212> TYPE: PRT
<213> ORGANISM: Artificial Sequence
<220> FEATURE:
<223> OTHER INFORMATION: 5' end amino acid sequence of PAM

<400> SEQUENCE: 10

Thr Thr Thr Val
1

<210> SEQ ID NO 11
<211> LENGTH: 4
<212> TYPE: PRT
<213> ORGANISM: Artificial Sequence
<220> FEATURE:
<223> OTHER INFORMATION: 3' end amino acid sequence of PAM

<400> SEQUENCE: 11

Val Ala Ala Ala
1

<210> SEQ ID NO 12
<211> LENGTH: 10
<212> TYPE: DNA
<213> ORGANISM: Artificial Sequence
<220> FEATURE:
<223> OTHER INFORMATION: PolyC

<400> SEQUENCE: 12
cccccccccc                                                                10

<210> SEQ ID NO 13
<211> LENGTH: 42
<212> TYPE: RNA
<213> ORGANISM: Artificial Sequence
<220> FEATURE:
<223> OTHER INFORMATION: Os_crRNA

<400> SEQUENCE: 13
uaauuucuac uaaguguaga uggaguggug acucgauaau ga                            42

<210> SEQ ID NO 14
<211> LENGTH: 42
<212> TYPE: RNA
<213> ORGANISM: Artificial Sequence
<220> FEATURE:
<223> OTHER INFORMATION: Ro_crRNA

<400> SEQUENCE: 14

```
uaauuucuac uaaguguaga uaauaaucga uucgaucaaa au                    42

<210> SEQ ID NO 15
<211> LENGTH: 42
<212> TYPE: RNA
<213> ORGANISM: Artificial Sequence
<220> FEATURE:
<223> OTHER INFORMATION: Ce_crRNA

<400> SEQUENCE: 15
uaauuucuac uaaguguaga uugcaccuga ugauuuucua cg                    42

<210> SEQ ID NO 16
<211> LENGTH: 371
<212> TYPE: DNA
<213> ORGANISM: Cervus elaphus

<400> SEQUENCE: 16
gaagtgatgg ttgctgaggg cagattgaag tttacaggtg atatttagaa tctactgtca    60
aaacttgggg cgggctgggg ccaggattga caaggaagtt taaaacactt gccaactaga   120
attttaacat ctcaggagga ctgctaaatt agcagagaga tttttcaccc agatctcatt   180
accaggccta ttaaaacaat ccccgttgca cactgtacta cgcattacgt agaaaatcat   240
caggtgcata aaggtgtacc ttgtttcata attagggga gatgcatagt ccagctacca    300
tgaaagagct aatggcatat ttctttgggg cttttcctca tctttaatta aagatactta   360
ccataataaa t                                                       371

<210> SEQ ID NO 17
<211> LENGTH: 403
<212> TYPE: DNA
<213> ORGANISM: Rangifer tarandus

<400> SEQUENCE: 17
tagcagaagt gatggttgct gagggcagat tgaagtttac aggtgatatt tagaatcgac    60
tgtcagaact tggggcaggc tggggccagg attgacgagg aagtttaaaa cacttgccaa   120
ctagaatttt aacatctcag gaggactgct aaattagcag agagatttt  cacccagatc   180 tcattaccag gcctgttaaa acaatccccg ttgcacactg tactatgcat tacctagaag   240
gttgtcaggt gcataaaggt gtaccgtgtt tcataattag ggggagatgc atcggccagc   300
taccatgaaa gagctgatgg catatttctt cggggctttt cctcatcttt aattaaaaat   360
acttaccata ataatggga ccagttcttc ctaggattct taa                     403
```

METHOD FOR IDENTIFYING SPECIES OF EUKARYOTE ON BASIS OF WHOLE GENOME ANALYSIS, AND USE THEREOF

RELATED APPLICATION

The present application is a national stage application under 35 U.S.C. § 371 of International Application No. PCT/CN2022/083950, filed Mar. 30, 2022. The above referenced application is hereby incorporated by reference.

TECHNICAL FIELD

The present application relates to the technical field of eukaryotic species identification, and specifically relates to a method of eukaryotic species identification on the basis of whole-genome analysis and use thereof.

BACKGROUND

Species identification accompanies the entire history of human development, and it is closely related to natural exploration, social development and scientific research. Although human beings have not yet been able to identify all life on the earth, the continuous development on identification methods has strengthened our understanding and realization to other lives. Numerous scientific researchers have always been committed to the identification and classification of diverse, widely distributed, complex and difficult-to-distinguish species. In the early stage, species identification is mainly performed based on phenotypes of the species such as morphological features, chemical compositions, etc., but the phenotypes cannot reflect the fundamental reasons of the differences among species due to the fact that the phenotypes are affected by factors such as environment, growth stage, etc. During this period, the continuous improvement of DNA sequencing technique in reads and accuracy facilitates the sequencing and analysis of species at the level of whole genome. Along with the explosive growth of the number of species with whole-genome data, species identification strategies on the basis of whole genome analysis become possible. As the carrier carrying all the genetic information of species, the whole genome reveals the fundamental reasons that a species distinguishes from other species and shows specificity. Therefore, the new identification method based on the whole genome also represents the future development direction on species identification. At the same time, the rapid development of bioinformatics and the identification foundation of molecular biology have also provided strong support for the achievement of species identification based on whole genome data. With the continuous development of molecular biology identification methods such as DNA barcode technology, different DNA barcodes available within a certain applicative range have been found; meanwhile, with the continuous iteration of sequencing technique and the development of computer hardware and software, genome analysis capabilities have also been greatly enhanced, both of which provide strong support for the achievement of species identification at the level of whole-genome.

Gene editing is a genetic engineering means used to artificially modify the genome of organisms. The technology currently mainly uses the following nucleases: zinc finger nucleases (ZFNs), transcription activator-like effector nucleases (TALEN) and Clustered regularly interspaced short palindromic repeats (CRISPR)/CRISPR-associated proteins (CRISPR/Cas). Wherein, the CRISPR/Cas system is a new generation of genome editing technique, which can recognize specific sequences to achieve the purpose of site-specific editing. Jennifer A. Doudna, Feng Zhang, and Jin Wang and others have successively developed methods such as DETECTR, SHERLOCK, and HOLMES, and successfully applied them to genome editing of viruses, bacteria, and eukaryotes. For example, in the field of plant biotechnology, gene editing means are mainly used to engineer plant genomes as new breeding technology to develop plant varieties with new properties (for example, see the records in Kangquan Yin et al., Progress and prospects in plant genome editing, Nature Plants, 3, 17107 (2017)).

At present, the prior art is mainly to screen the sequence that can distinguish a certain species in specific gene functional regions. Due to the small gene database available for screening, the target sequences that can be obtained are extremely finite, resulting in insufficient specificity of the target sequences and being prone to off-target errors and so on, which cannot well meet the needs for identification of different species. In particular, it is difficult to meet the needs for the identification of related species with extremely similar or even the same sequence in a specific region. The whole genome, which comprises all the genetic information of an organism, is an ideal database for species identification. Screening species-specific sequences through whole genome alignment and detecting the same are the future development direction on species identification.

SUMMARY OF THE INVENTION

To this end, the present application proposes a method of eukaryotic species identification on the basis of whole genome analysis. The method of the present application (hereinafter also referred to as a GA method) is based on Genome analysis to find a specific target sequence library that can accurately identify species, especially meet the distinguishing between the species being identified and the related species, and accurately identify the above specific sequences through the use of a variety of detection means including but not limited to genome editing, sequencing, etc., so as to achieve accurate identification of species. Compared to the prior art, the GA method of the present application screens and obtains a specific target sequence library that only is present in this species from whole genome of a species in bulk via methods of bioinformatics analysis, also considers the risk of errors such as off-target and improves the accuracy of species identification, so as to ultimately achieve accurate judgment on the identification of eukaryotic species.

The present application relates to a method of eukaryotic species identification based on whole genome analysis, comprising:
i) constructing a small-fragment genome library based on whole genome sequences of the species being identified;
ii) screening sequences in the small-fragment genome library selectively to obtain an extensive candidate target sequence library based on the needs of subsequent detecting or according to whole-genome annotation files and the species sequence information included in a database and the like;
iii) aligning the sequences in the small-fragment genome library or the extensive candidate target sequence library with whole genome sequences of related species, and selecting specific sequences only present in the species being identified to construct a specific target sequence library, based on the whole genome sequences of the related species of the species being identified;

iv) conducting species identification of eukaryotic samples based on selected specific target sequences. The genomic DNA of the eukaryotic samples to be detected is obtained, and the genomic DNA is detected whether it comprises the sequence in the specific target sequence library, thereby determining the identity of the samples to be detected and the species being identified. If the sequence in the specific target sequence library is detected, it is determined that the eukaryotic samples have identity with the species being identified, and vice versa, the eukaryotic samples have no identity.

In some preferred embodiments, in i), the whole genome sequences of the species being identified are divided into (L−K+1) fragments with length K to construct the small-fragment genome library, and the copy number of each fragment therein is calculated, and then the genome location of each fragment is determined by aligning each fragment with the whole genome sequences in order to facilitate better sequence alignment in subsequent steps, wherein L represents the length of the whole genome sequences and K represents the length of the fragments in the library.

In some preferred embodiments, in i), the species being identified may be any species in eukaryotes. As an example, the species being identified derives from different kingdoms of organisms such as animals, plants, fungi, etc., respectively.

The whole genome sequences of the species being identified herein can be obtained from known public databases or by whole genome sequencing via conventional methods.

In ii), the sequences in the small-fragment genome library are screened, enabling extract extensive candidate target sequences from the range of whole genome of the species being identified, rather than being limited to a specific region, so that the target sequences obtained are widely distributed, which contribute to eliminating risks such as off-target subsequently.

In some preferred embodiments, in ii), PAM motif is detected for each fragment in the small-fragment genome library, and the sequences with PAM are extracted to construct the extensive candidate target sequence library. PAM (protospacer adjacent motif) herein can be determined by the skilled in the art based on the genome editing system employed for subsequent detection of specific sequences, for example, when using CRISPR/Cas12a system for the subsequent detection, the PAM of TTTV (SEQ ID NO: 10) at 5' end or VAAA (SEQ ID NO: 11) at 3' end can be selected.

In iii), preferably, before being aligned with the whole genome sequences of the related species, the sequences in the small-fragment genome library or the extensive candidate target sequence library can be aligned with multiple (e.g., all) known genome sequences of the species being identified, and the sequences that can be exactly matched to the multiple known genome sequences of the species being identified are screened from the small-fragment genome library or the extensive candidate target sequences, and a primary candidate target sequence library of the species being identified is constructed. Subsequently, the primary candidate target sequence library is aligned with the whole genome sequences of the related species, and the sequences that are only present in the species being identified are selected to construct a specific target sequence library.

In iii), it is preferable to select the sequences only present in the species being identified within the regions with high intra-species conservation and large inter-species difference to construct a specific target sequence library. In view of the off-target effect, it is preferable to select a sequence with at least n base differences from the whole genome sequences of the related species (e.g., an adulterant), wherein n≥3. Preferably, the specificity of the target sequence can be further improved by increasing the n value, or the target sequences within a predefined number range can be screened by adjusting the n value.

In the present disclosure, in iii), preferably, the specific target sequence library can be constructed by selecting a plurality of different sequences that are only present in the species being identified, so as to be used in subsequent experiments to determine the identity of the sample to be detected and the species being identified.

In the present disclosure, the eukaryotic sample to be detected may be a sample from any eukaryote, such as a sample from an animal, plant, or fungus. As an example, the eukaryotic sample to be detected may be a sample from *Ophiocordyceps sinensis*, *Rheum officinale*, *Cervus elaphus*, *Cordyceps militaris*, *Rheum palmatum* or *Rangifer tarandus*. In some embodiments, the eukaryotic sample to be detected is a sample derived from a single species source or a mixture of samples derived from multiple species sources.

In some preferred embodiments, the species being identified is *Ophiocordyceps sinensis* from the Fungi Kingdom, and in iii), the specific target sequence is a nucleotide sequence set forth in SEQ ID NO: 1.

```
SEQ ID NO: 1:
TTTGGGAGTGGTGACTCGATAATGA.
```

In some preferred embodiments, the species being identified is *Rheum officinale* from the Plant Kingdom, and in iii), the specific target sequence is a nucleotide sequence set forth in SEQ ID NO: 2.

```
SEQ ID NO: 2:
AATATGGTTATGTTATATTAATAAA.
```

In some preferred embodiments, the species being identified is *Cervus elaphus* from the Animal Kingdom, and in iii), the specific target sequence is a nucleotide sequence set forth in SEQ ID NO: 3.

```
SEQ ID NO: 3:
TTTATGCACCTGATGATTTTCTACG.
```

In the present disclosure, in iv), regarding the detection, any detection techniques/means known in the art for the recognition of a specific sequence can be used. In some preferred embodiments, in iv), the sequence recognition means such as gene editing systems and sequencing can be used for the detection to determine whether the specific target sequence is present in the sample to be detected.

In some preferred embodiments, in iv), in order to make detection simpler and more direct, and maintain high sensitivity at the same time, a genome editing system, preferably a CRISPR/Cas system (such as CRISPR/Cas9 system, CRISPR/Cas12a system, CRISPR/Cas12b system, and CRISPR/Cas13 system) with a fluorescent signal molecule is used for the detection.

In the present disclosure, in iv), before conducting the detection, a tool library (such as a crRNA library, and a primer library) that matches the specific target sequence is pre-constructed based on the different techniques used in the sequence detection of the genomic DNA (including but not limited to gene editing technique, sequencing technique, etc.). In a further preferred embodiment, in iv), a genome editing system is used for the detection, and a tool library of CRISPR RNA (crRNA) and optional tracr RNA that match the specific target sequence is pre-constructed. In other preferred embodiments, in iv), sequencing is used for the detection, and a tool library of primer pairs that match the specific target sequence is pre-constructed.

In some preferred embodiments, the species being identified is *Ophiocordyceps sinensis*, and in iv), the following primer pair is used for the detection:

```
ITS4F:
                                   (SEQ ID NO: 4)
5'-GGAAGTAAAAGTCGTAACAAGG-3';

ITS5R:
                                   (SEQ ID NO: 5)
5'-TCCTCCGCTTATTGATATGC-3'
```

In some preferred embodiments, the species being identified is *Rheum officinale*, and in iv), the following primer pair is used for the detection:

```
Ro_1F:
                                   (SEQ ID NO: 6)
5'-CCAAATTGCCCGAAGCCTATG-3';

Ro_1R:
                                   (SEQ ID NO: 7)
5'-ATCGCTTTCCGACCCACAAT-3'
```

In some preferred embodiments, the species being identified is *Cervus elaphus*, and in iv), the following primer pair is used for the detection:

```
Ce_17F:
                                   (SEQ ID NO: 8)
5'-AGCAcervus elaphusTTGCTG-3';

Ce_17R:
                                   (SEQ ID NO: 9)
5'-AAGAATCCTAGGAAGAACTGGT-3'
```

In a further preferred embodiment, it is possible to select to perform thio-modification at both ends of the primer sequence, thereby further improving the amplification efficiency and detection sensitivity.

In the present disclosure, as an example, the desired genome editing system at least includes room-temperature amplification reagent, buffer, Cas protein, crRNA, nuclease-free water, and fluorescent signal molecule (such as ssDNA fluorescent reporter gene). For example, using the genomic DNA of the biological sample to be detected as the substrate, the above-mentioned desired genome editing system is used for detection. If it is identified that a species-specific target sequence is present, the reaction system generates fluorescence. When there is a significant difference between the measured fluorescence value and the blank control, it is determined that the sample to be detected has identity with the species being identified, and vice versa, the sample to be detected has no identity with the species being identified.

In the present disclosure, room-temperature amplification reagent can be any known amplification reagent selected by the skilled in the art according to the actual situation, and the buffer and Cas protein can be determined according to the genome editing system used. Specifically, taking CRISPR/Cas12a system as an example, ERA amplification reagent, NEBuffer 2.1 and Lba Cas12a (Cpf1) can be selected, and the fluorescent signal molecule Poly_C_FQ (5'-FAM-CCCCCCCCCC (SEQ ID NO: 12)-BHQ-3') can be selected. After adding crRNA, nuclease-free water and genomic DNA of the sample to be detected, the amplification reaction is conducted at the bottom of the tube, and the detection reagents (NEBuffer 2.1, Lba Cas12a, crRNA and nuclease-free water) react on the tube cap. As an example, detection is conducted using CRISPR/Cas12a system with the reaction system shown in Table 1 below. After the reaction system is incubated at 40° C. for 20 minutes, the detection reagents at tube cap is settled at the bottom by short centrifugation, and all reagents are fully mixed and incubated at room temperature for 10 minutes. 4 μL of Poly_C_FQ (400 nM) is mixed with the above system, and then incubated at 37° C., and the fluorescence values are detected at 0, 3, 6, 9, 12, 15, 25, 35, 45 and 60 minutes respectively by a microplate reader at λex 483 nm/λem 535 nm (these wavelengths can be determined according to the selected fluorescence signal molecule). If there is a significant difference between the detection results and that of the blank control (P<0.01), it can be determined that the sample to be detected has identity with the species being identified, and vice versa, it has no identity with the species being identified.

TABLE 1

| Exemplary reaction system using CRISPR/Cas12a system | |
| --- | --- |
| Components | Volume |
| ERA amplification reagent | 48 μL |
| Genomic DNA of the sample to be detected | 2 μL |
| 10× NEBuffer 2.1 | 10 μL |
| Lba Cas12a (Cpf1) | 2 μL (20 nM) |
| crRNA | 3.3 μL (300 nM) |
| Nuclease-free water | 30.7 μL |
| Poly_C_FQ | 4 μL (400 nM) |

The method described above can be used for species identification of eukaryotic samples in different application scenarios, which comprises: performing the method described above for the species being identified, and determining the identity between the sample to be detected and the species being identified based on the fluorescence detection results.

In one embodiment, the present application relates to use of the species identification method above in constructing a target sequence library for eukaryotic species identification, wherein the species being identified is selected and one or more specific target sequences of the species being identified are obtained by screening according to the species identification method above; one or more specific target sequences of the species being identified are combined to construct the target sequence library.

Alternatively, the present application relates to a method of constructing a specific target sequence library for eukaryotic species identification, comprising:
  a) selecting the species being identified, and screening one or more specific target sequences of the species being identified according to the species identification method described above;
  b) combining one or more specific target sequences of the species being identified to construct the specific target sequence library.

Alternatively, the present application relates to a method of constructing a tool library for detecting specific target sequences of eukaryotic species identification, comprising:

A) selecting the species being identified, and constructing the target sequence library according to the method of constructing a specific target sequence library described above;
B) constructing a tool library that matches the specific target sequence (including but not limited to crRNA library, primer library, etc.), based on the technology used for the detection (according to the diversity of sequence detection methods, it may include but is not limited to gene editing, sequencing technique, etc.).

Alternatively, the present application relates to a method of distinguishing Chinese medicinal materials from their corresponding adulterants, comprising:
I) using the Chinese medicinal materials or adulterants as the species being identified, and screening the specific target sequences according to the species identification method described above.;
II) obtaining the genomic DNA of a medicinal sample to be detected, and detecting whether the genomic DNA comprises the specific target sequence, thereby determining the identity of the medicinal sample to be detected with the Chinese medicinal materials or the adulterants.

Alternatively, the present application relates to a method for safety detection of food, medicament or health product, comprising:
1) employing eukaryotes for food use, eukaryotes for medicament use, or eukaryotes for health product use as the species being identified, and screening specific target sequences according to the species identification method described above;
2) obtaining the genomic DNA of the food, medicament or health product to be detected, and detecting whether the genomic DNA comprises the specific target sequence to determine the identity between the eukaryotic sample and the species being identified. Through this detection, food, medicament and health product derived from counterfeit and inferior biological species can be found, so as to ensure the safety of food, medicament and health product.

The present application relates to a species-specific target sequence, which is:
a species-specific target sequence for species identification of *Ophiocordyceps sinensis*, which is a nucleotide sequence set forth in SEQ ID NO: 1:
a species-specific target sequence for species identification of *Rheum officinale*, which is a nucleotide sequence set forth in SEQ ID NO: 2; or
a species-specific target sequence for species identification of *Cervus elaphus*, which is a nucleotide sequence set forth in SEQ ID NO: 3.

The present application relates to a primer pair for amplifying species-specific target sequences of eukaryotes, comprising:
the primer pair of Ro_1F: 5'-CCAAAT-TGCCCGAAGCCTATG-3' (SEQ ID NO: 6) and Ro_1R: 5'-ATCGCTTTCCGACCCACAAT-3' (SEQ ID NO:7) when the eukaryote is *Rheum officinale*; or
the primer pair of Ce_17F: 5'-AGCAGAAGT-GATGGTTGCTG-3' (SEQ ID NO: 8) and Ce_17R: 5'-AAGAATCCTAGGAAGAACTGGT-3' (SEQ ID NO: 9) when the eukaryote is *Cervus elaphus*.

When using the method described herein for species identification, it can distinguish the species being identified from the related species thereof, so as to accurately achieve the accurate identification of eukaryotes at the species level. This method can play a positive role in the identification of Chinese medicinal material adulterants, food safety, and the safety of medicament and health product. The method has strong specificity, high sensitivity and good reproducibility, and can achieve rapid species identification of biological samples without relying on large-scale professional devices, and thus can have broad application prospects.

Hereinafter, exemplary embodiments of the present application are further illustrated in combination with drawings to illustrate the purpose, technical features and technical effects of the solutions of the present application, but the solutions of the present application may also have other undescribed features, advantages, etc.

BRIEF DESCRIPTION OF THE DRAWINGS

In order to more clearly illustrate the technical solutions in the present disclosure or related techniques, the drawings required to be used in the examples or related technical description will be briefly introduced hereinafter. The following drawings are only examples of the present disclosure, and the protection scope of the present application is not limited hereto.

EMBODIMENTS OF THE INVENTION

Hereinafter, the present application is described in details through examples, but it does not mean any adverse limitation to the present application. This disclosure has described the present application in details, and also disclosed specific embodiments thereof. For the skilled in the art, it will be obvious to make various modifications and improvements on the specific embodiments of the present application without departing from the spirit and scope of the present application.

Unless defined otherwise, the technical and scientific terms used herein have the same meanings as commonly understood by the person of ordinary skill in the art to which this disclosure belongs, which can be seen in, for example, Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, NY 1989); Current Protocols in Molecular Biology or Current Protocols in Immunology, John Wiley & Sons, New York, N.Y. (2009); Perbal, A Practical Guide to Molecular Cloning (1984).

Unless definitely indicated otherwise in the context thereof, the term "or" herein intends to include "and", and vice versa. Unless stated otherwise, a singular term herein encompasses the plural form thereof, and vice versa.

Unless stated otherwise, the terms "comprise", "comprises" and "comprising" or equivalents thereof (such as "contain", "containing", "include" and "including") herein are open-ended mode expressions and should be understood as "including but not limited to", which mean that other unspecified elements, components and steps may be included in addition to those already listed.

Unless stated otherwise, the term "whole genome" herein encompasses not only the entire genome sequences of an organism, but also the genome of organelles (such as the chloroplast genome).

EXAMPLES

Figure 1:
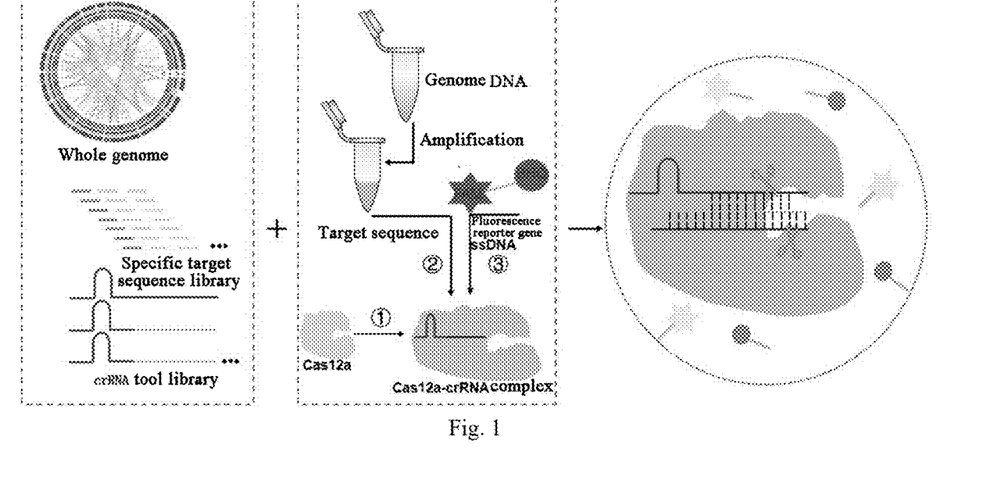
FIG. 1 is an exemplary flow chart showing the GA method of the present disclosure.
Figure 2:
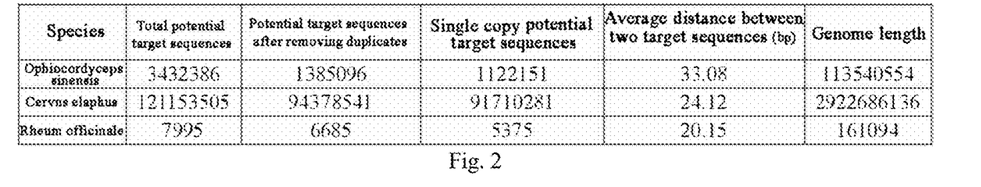
FIG. 2 is a table showing the information related to candidate target sequences of different species being identified from the Fungi, Animal, and Plant Kingdoms.

FIG. 1 shows an exemplary flow chart of the GA method of the present application. The GA method is further set forth through examples in combination with the identification process of *Ophiocordyceps sinensis, Rheum officinale*, and *Cervus elaphus*, but the scope of the present application is not limited hereto.

The experimental methods that do not indicate specific conditions in the following examples are implemented in accordance with conventional conditions. Unless stated otherwise, the reagents, materials or devices used in the following examples, the manufacturers of which are not indicated, are conventional products commercially available.

Example 1: Constructing a Small-Fragment Genome Library of *Ophiocordyceps sinensis* and Obtaining Extensive Candidate Target Sequences Therefrom 1.1 Constructing a Small-Fragment Genome Library of *Ophiocordyceps sinensis*

The whole genome data (assembly accession no.: GCA_002077885.1) of *Ophiocordyceps sinensis* used as the species being identified were downloaded from the NCBI database, and the whole genome sequences of *Ophiocordyceps sinensis* were divided into (L−25+1, L=whole genome sequence length) fragments with a length of 25 bp using Jellyfish (v1.1.12) to construct a small-fragment genome library of *Ophiocordyceps sinensis*.

1.2 Obtaining Extensive Candidate Target Sequences

The sequences with PAM were extracted from the above constructed small-fragment genome library of *Ophiocordyceps sinensis* (5' end of the PAM has TTTV (SEQ ID NO: 10) or 3' end thereof has VAAA (SEQ ID NO: 11)). Wherein 3,432,386 candidate target sequences with PAM were screened from the whole genome sequences of *Ophiocordyceps sinensis*, and 1,385,096 extensive candidate target sequences with PAM were obtained after removing duplicates.

Example 2: Screening the Specific Target Sequence of *Ophiocordyceps sinensis* for Species Identification 2.1 Screening Specific Target Sequence In the present disclosure, the target sequences were screened within the range of the genome of the species being identified, and it gave priority to screening the target sequences in regions with high intra-species conservation and strong inter-species difference. The target sequences had 3 or more base mismatches with the corresponding sequences of the related species. If there were multiple target sequences that met the aforementioned conditions at the same time, one or more target sequences with more copy numbers were selected preferably.

The specific screening steps were as follows: (1) Data preparation: Downloading all disclosed genome sequences of *Ophiocordyceps sinensis* and genome sequences of adulterant thereof, *Cordyceps militaris*, from the NCBI database; (2) Screening of *Ophiocordyceps sinensis* primary candidate target sequences: Aligning the extensive candidate target sequences obtained in Example 1 with all the disclosed genome sequences of *Ophiocordyceps sinensis* downloaded from the database by using Bowtie (v1.1.0), screening the sequences that could completely match all the disclosed genome sequences of *Ophiocordyceps sinensis* from the extensive candidate target sequences, and constructing the primary candidate target sequence library of *Ophiocordyceps sinensis*; (3) Screening of inter-species specific candidate target sequence of *Ophiocordyceps sinensis*: Aligning the primary candidate target sequence library obtained in (2) with the genome sequences of the adulterant, *Cordyceps militaris*, by using Bowtie (v1.1.0), and screening one sequence that did not have 3 or less base mismatches with the adulterants from the primary candidate target sequence library as the specific target sequence.

Figure 3:
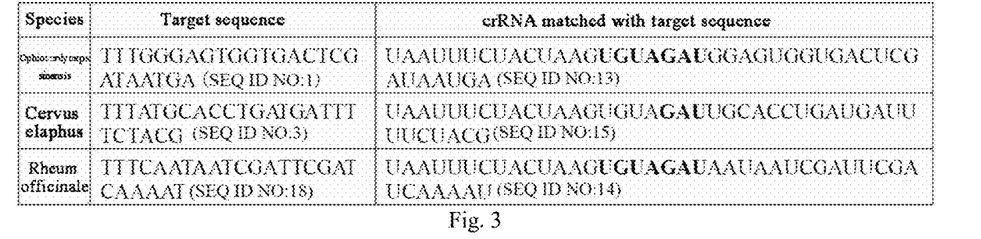
FIG. 3 shows the specific target sequences of *Ophiocordyceps sinensis, Rheum officinale*, and *Cervus elaphus*, as well as the crRNAs matched to each specific target sequence.
Figure 4:
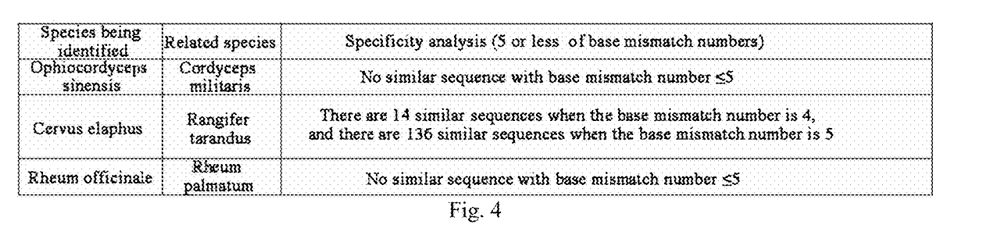
FIG. 4 is a diagram of specificity analysis for the specific target sequences of the species being identified.

The specific target sequence obtained above was named as Os_target (SEQ ID NO: 1), as shown in FIG. 3. The specific analysis results of the specific target sequence in the adulterants were shown in FIG. 4.

2.2 Designing crRNA that Matched the Specific Target Sequence

According to the genome editing system (CRISPR/Cas12a system) used in subsequent experiments and the crRNA design principles, the crRNA matching Os_target was designed and named as Os_crRNA (SEQ ID NO: 13), as shown in FIG. 3.

Example 3: Identification of *Ophiocordyceps sinensis* Via GA

In order to determine whether the specific target sequence of the species being identified screened in Example 2 could specifically and accurately reflect the identity between the sample to be detected and the species being identified, the species identification of the samples was then conducted based on genomic DNA of each of *Ophiocordyceps sinensis* and *Cordyceps militaris* samples as well as a mixture thereof.

3.1 Genomic DNA Extraction and Amplification of *Ophiocordyceps sinensis* and *Cordyceps militaris* Samples A sample of *Ophiocordyceps sinensis* (collected from Beijing) was taken, added into liquid nitrogen and ground thoroughly into a powder, and the total DNA of each sample was then extracted using TIANamp Genomic DNA kit in accordance with the instructions of the kit provided by TIANGEN. The integrity of the total DNA of each sample obtained was detected by 0.8% agarose gel electrophoresis, and then the purity and concentration thereof were detected with a Nanodrop 2000C spectrophotometer.

Meanwhile, the genomic DNA of *Cordyceps militaris* sample was extracted in accordance with the above steps, and the integrity of the total DNA of each sample was detected by 0.8% agarose gel electrophoresis.

As the target sequence of *Ophiocordyceps sinensis* was located in the ITS region of the genome thereof, the universal primers for this region were used for experiments; in order to improve the stability of the reaction, operations including but not limited to thio-modification at both ends of the primers could be used, and the specific sequence information thereof was as follows:

```
ITS4F:
                                          (SEQ ID NO: 4)
5'-G*G*AAGTAAAAGTCGTAACAA*G*G-3';

ITS5R:
                                          (SEQ ID NO: 5)
5'-T*C*CTCCGCTTATTGATAT*G*C-3'
```

3.2 Species Identification of the Samples to be Detected Based on Genome Editing Technique The Os group (group of *Ophiocordyceps sinensis* sample), Cm group (group of *Cordyceps militaris* sample), Os+Cm group (group of *Ophiocordyceps sinensis*+*Cordyceps militaris* samples) and CK (blank control) group were set up, respectively.

In the following reaction system for species identification, Os_crRNA was used as the crRNA, and for each sample group to be detected, the genomic DNA of the samples (*Ophiocordyceps sinensis*, *Cordyceps militaris*, or a mixture thereof) in each group extracted above was used as the DNA substrate. The experiment was conducted using EnGen Lba Cas12a (Cpf1) from NEB, and the total volume of the reaction system was 100 µL: 10 µL of 10×NEBuffer 2.1, 2 µL of Lba Cas12a (20 nM), 3.3 µL of crRNA (300 nM), 3 µL of DNA substrate (10 ng/µL), 47 µL of ERA amplification reagent, 4 µL of Poly_C_FQ (400 nM) and 30.7 µL of nucleus-free H2O.

The ERA amplification reagent and DNA substrate in the above reaction system were firstly added into the bottom of the 1.5 mL centrifuge tube; NEBuffer 2.1, Lba Cas12a, Os_crRNA and nuclease-free H2O were added to the inner side of the tube cap and incubated at 40° C. for 20 minutes, and then the reagents in the tube cap were quickly transferred to the bottom of the tube by simple centrifugation or gravity, followed by continuing to incubate the same at 37° C. for 10 minutes; and then Poly_C_FQ was added thereto, incubated at 37° C., and the fluorescence at λex 483 nm/λem 535 nm was detected with a microplate reader at 0, 3, 6, 9, 12, 15, 25, 35, 45 and 60 minutes, respectively.

Figure 5:
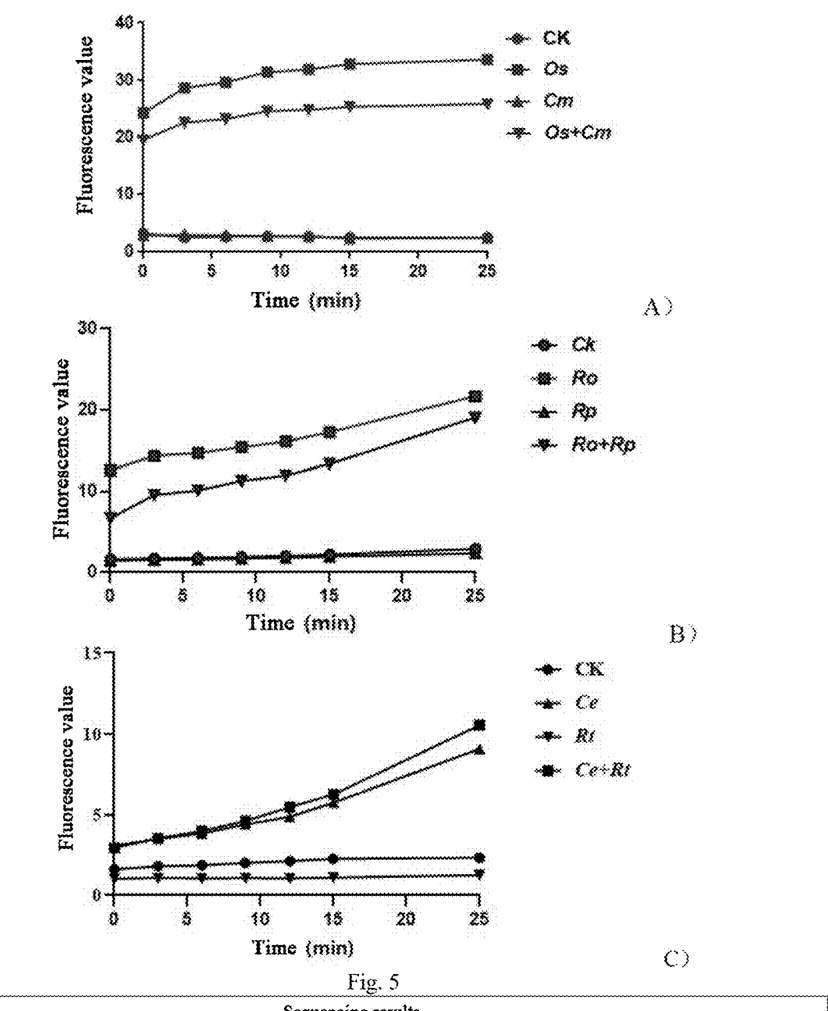
FIG. 5 shows the fluorescence detection results of *Ophiocordyceps sinensis* sample (panel A), *Rheum officinale* sample (panel B) and *Cervus elaphus* sample (panel C) and adulterants thereof.

Panel A in FIG. 5 showed the fluorescence detection results of each sample group to be detected. As shown in panel A, the Os group generated fluorescence signal, and the fluorescence value reached to the maximum at 25 minutes and was maintained, which had statistically significant difference from the CK group (P<0.01). The Cm group was consistent with the CK group, neither of which generated fluorescence signal, and there was no significant difference in fluorescence value of the Cm group from that of the CK group (P>0.01). Meanwhile, the mixed sample group (i.e., the Os+Cm group) could also generate strong fluorescence signal due to comprising the sample of *Ophiocordyceps sinensis*, the fluorescence value of which was statistically significantly different from the CK group (P<0.01). It can be seen that the method of the present invention can specifically and accurately reflect whether the sample to be detected had identity with the species being identified.

Example 4: Constructing a Small-Fragment Genome Library of *Rheum officinale* and Obtaining Extensive Candidate Target Sequences Therefrom 4.1 Constructing a Small-Fragment Genome Library of *Rheum officinale*

The chloroplast genome data (assembly accession no.: MZ998517) of *Rheum officinale* used as the species being identified were downloaded from the NCBI database, and the chloroplast genome sequences of *Rheum officinale* were divided into (L−25+1, L=chloroplast genome sequence length) fragments with a length of 25 bp using Jellyfish (v1.1.12) to construct a small-fragment genome library of *Rheum officinale*.

4.2 Obtaining Extensive Candidate Target Sequences

The sequences with PAM were extracted from the above constructed small-fragment genome library of *Rheum officinale* (5' end of the PAM has TTTV (SEQ ID NO: 10) or 3' end thereof has VAAA (SEQ ID NO: 11)). Wherein 7,995 candidate target sequences with PAM were screened from the whole genome sequences of *Rheum officinale*, and 6,685 extensive candidate target sequences with PAM were obtained after removing duplicates.

Example 5: Screening the Specific Target Sequence of *Rheum officinale* for Species Identification 5.1 Screening Specific Target Sequence (1) Data preparation: Downloading all disclosed chloroplast genome sequences of *Rheum officinale* and chloroplast genome sequences of adulterant thereof, *Rheum palmatum*, from the NCBI database; (2) Screening of *Rheum officinale* primary candidate target sequences: Aligning the extensive candidate target sequences obtained in Example 4 with all the disclosed chloroplast genome sequences of *Rheum officinale* downloaded from the database by using Bowtie (v1.1.0), screening the sequences that could completely match all the disclosed chloroplast genome sequences of *Rheum officinale* from the extensive candidate target sequences, and constructing the primary candidate target sequence library of *Rheum officinale*; (3) Screening of inter-species specific candidate target sequence of *Rheum officinale*: Aligning the primary candidate target sequence library obtained in (2) with the chloroplast genome sequences of the adulterant, *Rheum palmatum*, by using Bowtie (v1.1.0), and screening one sequence that did not have 3 or less base mismatches with the adulterants from the primary candidate target sequence library as the specific target sequence.

The specific target sequence obtained above was named as Ro_target (SEQ ID NO: 2), as shown in FIG. 3. The specific analysis results of the specific target sequence in the adulterants were shown in FIG. 4.

5.2 Designing crRNA that Matched the Specific Target Sequence

According to the genome editing system (CRISPR/Cas12a system) used in subsequent experiments and the crRNA design principles, the crRNA matching Ro_target was designed and named as Ro_crRNA (SEQ ID NO: 14), as shown in FIG. 3.

Example 6: Identification of *Rheum officinale* Via GA

In order to determine whether the specific target sequence of the species being identified screened in Example 5 could specifically and accurately reflect the identity between the sample to be detected and the species being identified, the species identification of the sample was then conducted based on genomic DNA of each of *Rheum officinale* and *Rheum palmatum* samples as well as a mixture thereof.

6.1 Genomic DNA Extraction of *Rheum officinale* and *Rheum palmatum* Samples

According to the method described in Example 3, the genomic DNAs of *Rheum officinale* sample (collected from Mianning, Sichuan) and *Rheum palmatum* sample were extracted.

Based on the specific target sequence of *Rheum officinale* obtained in Example 5, the specific primers were designed, and the specific sequence information thereof was as follows:

```
Ro_1F:
                              (SEQ ID NO: 6)
5'-CCAAATTGCCCGAAGCCTATG-3';

Ro_1R:
                              (SEQ ID NO: 7)
5'-ATCGCTTTCCGACCCACAAT-3'
```

6.2 Species Identification of the Samples to be Detected Based on Genome Editing Technique The Ro group (group of *Rheum officinale* sample), Rp group (group of *Rheum palmatum* sample), Ro+Rp group (group of *Rheum officinale*+*Rheum palmatum* samples) and CK (blank control) group were set up, respectively. In the following reaction system for species identification, Ro_crRNA was used as the crRNA, and for each sample group to be detected, the genomic DNA of the samples (*Rheum officinale* sample, *Rheum palmatum* sample, or a mixture thereof) in each group extracted above was used as the DNA substrate.

The species identification of the above samples was conducted in accordance with the operating steps and reaction conditions described in section "3.2 Species identification of the samples to be detected based on genome editing technique" of Example 3.

Panel B in FIG. 5 showed the fluorescence detection results of each sample group to be detected. As shown in panel B, the Ro group generated fluorescence signal, and the fluorescence value reached to the maximum at 25 minutes and was maintained, which had statistically significant difference from the CK group (P<0.01). The Rp group was consistent with the CK group, neither of which generated fluorescence signal, and there was no significant difference in fluorescence value of the Rp group from that of the CK group (P>0.01). Meanwhile, the mixed sample group (i.e., the Ro+Rp group) could also generate strong fluorescence signal due to comprising the sample of *Rheum officinale*, the fluorescence value of which was statistically significantly different from the CK group (P<0.01). It can be seen that the method of the present invention can specifically and accurately reflect whether the sample to be detected had identity with the species being identified.

Example 7: Constructing a Small-Fragment Genome Library of *Cervus elaphus* and Obtaining Extensive Candidate Target Sequences Therefrom 7.1 Constructing a Small-Fragment Genome Library of *Cervus elaphus*

The whole genome data (assembly accession no.: GCA_910594005.1) of *Cervus elaphus* used as the species being identified were downloaded from the NCBI database, and the whole genome sequences of *Cervus elaphus* were divided into (L−25+1, L=whole genome sequence length) fragments with a length of 25 bp using Jellyfish (v1.1.12) to construct a small-fragment genome library of *Cervus elaphus*.

7.2 Obtaining Extensive Candidate Target Sequences

The sequences with PAM were extracted from the above constructed small-fragment genome library of *Cervus elaphus* (5' end of the PAM has TTTV (SEQ ID NO: 10) or 3' end thereof has VAAA (SEQ ID NO: 11)). Wherein 121,153,505 candidate target sequences with PAM were screened from the whole genome sequences of *Cervus elaphus*, and 94,378,541 extensive candidate target sequences with PAM were obtained after removing duplicates.

Example 8: Screening the Specific Target Sequence of *Cervus elaphus* for Species Identification 8.1 Screening Specific Target Sequence (1) Data preparation: Downloading all disclosed genome sequences of *Cervus elaphus* and genome sequences of adulterant thereof, *Rangifer tarandus*, from the NCBI database; (2) Screening of *Cervus elaphus* primary candidate target sequences: Aligning the extensive candidate target sequences obtained in Example 7 with all the disclosed genome sequences of *Cervus elaphus* downloaded from the database by using Bowtie (v1.1.0), screening the sequences that could completely match all the disclosed genome sequences of *Cervus elaphus* from the extensive candidate target sequences, and constructing the primary candidate target sequence library of *Cervus elaphus*; (3) Screening of inter-species specific candidate target sequence of *Cervus elaphus*: Aligning the primary candidate target sequence library obtained in (2) with the genome sequences of the adulterant, *Rangifer tarandus*, by using Bowtie (v1.1.0), and screening one sequence that did not have 3 or less base mismatches with the adulterants from the primary candidate target sequence library as the specific target sequence.

The specific target sequence obtained above was named as Ce_target (SEQ ID NO: 3), as shown in FIG. 3. The specific analysis results of the specific target sequence in the adulterants were shown in FIG. 4.

8.2 Designing crRNA that Matched the Specific Target Sequence

According to the genome editing system (CRISPR/Cas12a system) used in subsequent experiments and the crRNA design principles, the crRNA matching Ce_target was designed and named as Ce_crRNA (SEQ ID NO: 15), as shown in FIG. 3.

Example 9: Identification of *Cervus elaphus* Via GA

In order to determine whether the specific target sequence of the species being identified screened in Example 8 could specifically and accurately reflect the identity between the sample to be detected and the species being identified, the species identification of the sample was then conducted based on genomic DNA of each of *Cervus elaphus* and *Rangifer tarandus* samples as well as a mixture thereof.

9.1 Genomic DNA Extraction of *Cervus elaphus* and *Rangifer tarandus* Samples

According to the method described in Example 3, the genomic DNAs of *Cervus elaphus* sample (*Cervus elaphus* meat, collected from Fushun, Liaoning) and *Rangifer tarandus* sample (*Rangifer tarandus* meat) were extracted.

Based on the specific target sequence of *Cervus elaphus* obtained in Example 8, the specific primers were designed. In order to improve the stability of the reaction, operations including but not limited to thio-modification at both ends of the primers could be used, and the specific sequence information thereof was as follows:

```
Ce_17F:
                                      (SEQ ID NO: 8)
5'-A*G*CAGAAGTGATGGTTGC*T*G-3';

Ce_17R:
                                      (SEQ ID NO: 9)
5'-A*A*GAATCCTAGGAAGAACTG*G*T-3'
```

9.3 Detecting Samples Based on the Specific Target Sequence Using Genome Editing Technique The Ce group (group of *Cervus elaphus* sample), Rt group (group of *Rangifer tarandus* sample), Ce+Rt group (group of *Cervus elaphus*+*Rangifer tarandus* samples) and CK (blank control) group were set up, respectively. In the following reaction system for species identification, Ce_crRNA was used as the crRNA, and for each sample group to be detected, the genomic DNA of the samples (*Cervus elaphus* sample, *Rangifer tarandus* sample, or a mixture thereof) in each group extracted above was used as the DNA substrate.

The species identification of the above samples was conducted in accordance with the operating steps and reaction conditions described in section "3.2 Species identification of the samples to be detected based on genome editing technique" of Example 3.

Panel C in FIG. 5 showed the fluorescence detection results of each sample group to be detected. As shown in panel C, the Ce group generated fluorescence signal, and the fluorescence value reached to the maximum at 25 minutes and was maintained, which had statistically significant difference from the CK group (P<0.01). The Rt group was consistent with the CK group, neither of which generated fluorescence signal, and there was no significant difference in fluorescence value of the Rt group from that of the CK group (P>0.01). Meanwhile, the mixed sample group (i.e., the Ce+Rt group) could also generate strong fluorescence signal due to comprising the sample of *Cervus elaphus*, the fluorescence value of which was statistically significantly different from the CK group (P<0.01). It can be seen that the method of the present invention can specifically and accurately reflect whether the sample to be detected had identity with the species being identified.

Figure 6:
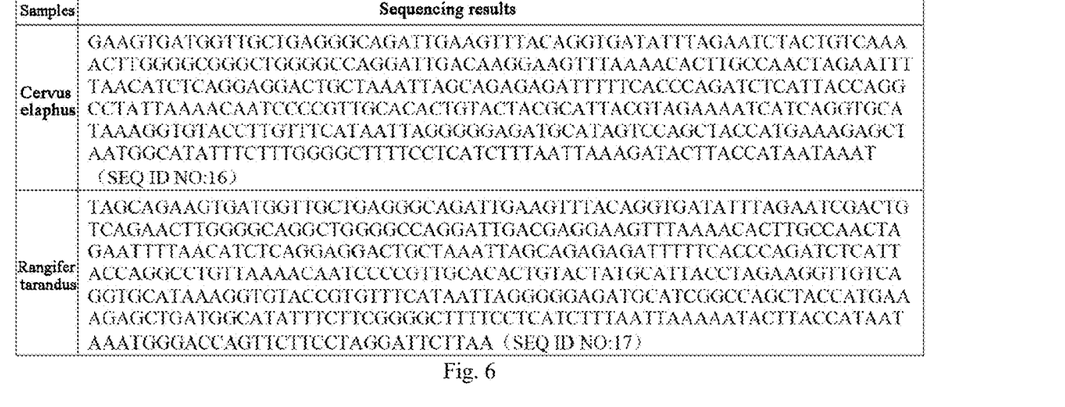
FIG. 6 shows the sequencing detection results of *Cervus elaphus* and the adulterant thereof which is *Rangifer tarandus*.

Example 10: Species Identification of *Cervus elaphus* and *Rangifer tarandus* Samples Based on Sequencing Technique In order to exemplarily illustrate that a variety of different sequence detection techniques can be used for species identification of eukaryotic samples, based on the specific target sequence of *Cervus elaphus* obtained in Example 8, the primer pair of Ce_17F and Ce_17R (SEQ ID NO: 8 and SEQ ID NO: 9) was used to specifically amplify the genomic DNAs of the *Cervus elaphus* and *Rangifer tarandus* samples to be detected obtained in Example 9, and the amplification product was sequenced. The result showed that when the sample to be detected was consistent with the species being identified, a sequence comprising the specific target sequence could be obtained in the sequencing result; when the sample to be detected was inconsistent with the species being identified, the specific target sequence could not be found in the sequencing result of the amplification product, as shown in FIG. 6. It can be seen that the method of the present invention can specifically and accurately reflect whether the sample to be detected had identity with the species being identified.

According to the results of the above Examples 3, 6, 9 and 10, it can be seen that the method of the present application can accurately identify the species of each group of samples comprising *Ophiocordyceps sinensis* sample (fungus), *Rheum officinale* sample (plant) and *Cervus elaphus* sample (animal), and can be used to clearly distinguish the quality products of medicinal materials (i.e., *Ophiocordyceps sinensis*, *Rheum officinale* and *Cervus elaphus*) from their respective common adulterants (i.e., *Cordyceps militaris*, *Rheum palmatum* and *Rangifer tarandus*).

The ordinary skilled in the art should understand that the discussion in any of the above examples is only exemplary and does not intend to imply that the protection scope of the present disclosure is limited to these examples; under the concept of the present disclosure, the above examples or the technical features in different examples can also be combined, the steps can be implemented in any order, and there are many other changes in different aspects of the examples of the present disclosure as described above, which are not provided in details for simplicity. The examples of the present application intend to encompass all such substitutions, modifications, and variations that fall within the broad scope of the attached claims. Therefore, any omission, modification, equivalent substitution, improvement, etc. made within the spirit and principle of the examples of the present disclosure shall be included within the protection scope of the present disclosure.

All patents, patent applications and other publications are hereby expressly incorporated herein by reference for the purpose of describing and disclosing. These publications are provided solely for their disclosure prior to the filing date of the present application. All statements as to the date or representation as to the contents of these documents is based on the information available to the applicants and does not constitute any admission as to the correctness of the dates or contents of these documents. Moreover, in any country, any reference to these publications herein does not constitute an endorsement that the publication becomes part of the common knowledge in the art.

What is claimed is:

1. A method of eukaryotic species identification based on whole genome analysis, comprising:
   i) dividing whole genome sequences of a species being identified into L−K+1 fragments with a length K to construct a small-fragment genome library, calculating a copy number of each fragment therein, and determining a genome location of each fragment by aligning each fragment with the whole genome sequences, wherein L is a length of the whole genome sequences, and the length K is a length of each fragment in the small-fragment genome library;
   ii) detecting a PAM (Protospacer Adjacent Motif) for each fragment in the small-fragment genome library, and extracting whole genome sequences the fragment with the PAM to construct an extensive candidate target sequence library, wherein the PAM includes one of a first nucleotide sequence set forth in SEQ ID NO: 10 at 5′ end or a second nucleotide sequence set forth in SEQ ID NO: 11 at 3′ end;
   iii) aligning sequences in the extensive candidate target sequence library with whole genome sequences of a related species, and selecting a plurality of different sequences only present in the species being identified within a region with intra-species conservation and inter-species difference to construct a specific target sequence library based on the whole genome sequences of the related species, wherein the plurality of different sequences only present in the species being identified are candidate target sequences with at least n base differences from whole genome sequences of at least one related species, wherein n is ≥3; and
   iv) obtaining a genomic DNA of a eukaryotic sample to be detected, and conducting species identification of the eukaryotic sample based on specific target sequences in the specific target sequence library, v) pre-constructing a crRNA that matches a specific target sequence, and vi) detecting whether the genomic DNA comprises the sequences in the specific target sequence library based on a CRISPR/Cas12a gene editing system, thereby determining an identity between the eukaryotic sample and the species being identified.

2. The method of claim 1, wherein, in i) and iv), the species being identified or the eukaryotic sample to be detected derives from animals, plants, or fungi.

3. The method of claim 2, wherein the eukaryotic sample to be detected is a sample derived from a single species or a mixture of samples derived from multiple species.

4. The method of claim 3, wherein the eukaryotic sample to be detected is from *Ophiocordyceps sinensis, Cordyceps militaris, Rheum officinale, Rheum palmatum, Cervus elaphus* or *Rangifer tarandus*.

5. The method of claim 1, wherein the species being identified is *Ophiocordyceps sinensis*, the specific target sequence is a nucleotide sequence set forth in SEQ ID NO: 1, and crRNA that matches the specific target sequence is set forth in SEQ ID NO: 13.

6. The method of claim 1, wherein the species being identified is *Rheum officinale*, the specific target sequence is a nucleotide sequence set forth in SEQ ID NO: 2, and crRNA that matches the specific target sequence is set forth in SEQ ID NO: 14.

7. The method of claim 1, wherein the species being identified is *Cervus elaphus*, the specific target sequence is a nucleotide sequence set forth in SEQ ID NO: 3, and crRNA that matches the specific target sequence is set forth in SEQ ID NO: 15.

8. A method of constructing a specific target sequence library for eukaryotic species identification, comprising:

a) selecting a species being identified, and screening one or more specific target sequences of the species being identified according to the method in claim 1; and b) combining the one or more specific target sequences of the species being identified to construct the specific target sequence library.

9. A method of constructing a tool library for detecting a specific target sequence of eukaryotic species identification, comprising:

A) selecting a species being identified and constructing a specific target sequence library according to the method of claim 8; and B) constructing the tool library that matches the specific target sequence, based on gene editing with CRISPR/Cas12a, wherein the tool library is a crRNA library.

10. A method of distinguishing Chinese medicinal materials from their corresponding adulterants, comprising:

I) using the Chinese medicinal materials or adulterants as a species being identified, and screening a specific target sequence according to the method in claim 1; and II) obtaining the genomic DNA of a medicinal sample to be detected, and detecting whether the genomic DNA comprises the specific target sequence based on a CRISPR/Cas12a gene editing system, thereby determining the identity between the medicinal sample to be detected and the Chinese medicinal materials or the adulterants.

* * * * *